(12) United States Patent
Stadelhofer (10) Patent No.: US 6,679,248 B2
(45) Date of Patent: Jan. 20, 2004

(54) DISCHARGE APPARATUS FOR MEDIA

(75) Inventor: Peter Stadelhofer, Singen (DE)

(73) Assignee: Ing. Erich Pfeiffer GmbH, Radolfzell (DE)

( * ) Notice: Subject to any disclaimer, the term of this patent is extended or adjusted under 35 U.S.C. 154(b) by 0 days.

(21) Appl. No.: 09/909,306

(22) Filed: Jul. 19, 2001

(65) Prior Publication Data
US 2002/0023641 A1 Feb. 28, 2002

(30) Foreign Application Priority Data
Jul. 27, 2000 (DE) .......................... 100 36 594

(51) Int. Cl.$^7$ ............................. A61M 11/00
(52) U.S. Cl. ................ 128/200.14; 128/203.15; 128/203.21
(58) Field of Search ............... 604/82, 83, 84, 604/85, 86, 87, 208, 211, 246; 222/82, 153.05, 319, 320, 386, 80; 128/200.14, 203.12, 203.15, 203.17, 203.21

(56) References Cited

U.S. PATENT DOCUMENTS

| | | | | |
|---|---|---|---|---|
| 1,393,720 A | * | 10/1921 | Lomas et al. ................ 604/210 |
| 2,581,182 A | * | 1/1952 | Fields .................... 128/203.15 |
| 3,756,390 A | * | 9/1973 | Abbey et al. ................ 206/219 |
| 4,175,704 A | * | 11/1979 | Cohen ........................ 239/320 |
| 4,394,863 A |   | 7/1983 | Bartner |
| 4,475,905 A | * | 10/1984 | Himmelstrup ............... 604/208 |
| 4,529,403 A |   | 7/1985 | Kamstra |
| 4,921,142 A | * | 5/1990 | Graf et al. .................. 222/162 |
| 4,962,868 A | * | 10/1990 | Borchard ................ 128/200.14 |
| 4,983,164 A | * | 1/1991 | Hook et al. .................. 604/139 |
| 5,080,649 A | * | 1/1992 | Vetter ........................ 604/191 |
| 5,143,211 A | * | 9/1992 | Miczka et al. ............... 206/219 |
| 5,232,457 A | * | 8/1993 | Grim .......................... 604/195 |
| 5,257,726 A | * | 11/1993 | Graf et al. ................... 222/320 |
| 5,277,334 A | * | 1/1994 | Malinconico ................. 222/36 |
| 5,281,198 A | * | 1/1994 | Haber et al. ................. 604/191 |
| 5,284,132 A | * | 2/1994 | Geier .................... 128/200.22 |
| 5,289,818 A | * | 3/1994 | Citterio et al. ......... 128/200.14 |
| 5,307,953 A | * | 5/1994 | Regan .......................... 222/82 |
| 5,318,544 A | * | 6/1994 | Drypen et al. .............. 604/210 |
| 5,364,350 A | * | 11/1994 | Dittmann .................... 604/416 |
| 5,427,280 A | * | 6/1995 | Fuchs ......................... 222/320 |
| 5,531,683 A | * | 7/1996 | Kriesel et al. .............. 604/416 |
| 5,569,192 A | * | 10/1996 | van der Wal ............... 604/135 |
| 5,637,087 A | * | 6/1997 | O'Neil et al. .................. 604/82 |
| 5,813,570 A | * | 9/1998 | Fuchs et al. .................. 222/82 |
| 5,817,055 A | * | 10/1998 | Ljungquist ................... 604/232 |
| 5,817,056 A | * | 10/1998 | Tanaka et al. ................. 604/84 |

(List continued on next page.)

FOREIGN PATENT DOCUMENTS

| | | |
|---|---|---|
| DE | 199 44 209 | 3/2001 |
| EP | 0 072 057 | 2/1983 |
| EP | 0 107 874 | 5/1984 |
| EP | 0 245 895 | 11/1987 |
| EP | 1066847 A1 | 10/2001 |
| FR | 2 506 161 | 11/1982 |
| GB | 1 449 986 | 9/1976 |
| WO | WO 91/10460 | 7/1991 |

Primary Examiner—Weilun Lo
Assistant Examiner—Michael G. Mendoza
(74) Attorney, Agent, or Firm—Quarles & Brady LLP (57) ABSTRACT

The invention relates to a discharge apparatus for media.

In the case of such discharge apparatuses the medium to be discharged is stored in a container, which has chambers separated from one another. Into each of the chambers is introduced at least one media component and the media components together form the medium to be discharged. The container is placed in a casing having a discharge opening for discharging the medium. An actuating means movable relative to the casing is provided. Through the actuation of the actuating means firstly a connection between the chambers of the container is produced.

24 Claims, 3 Drawing Sheets

U.S. PATENT DOCUMENTS

| | | | | |
|---|---|---|---|---|
| 5,935,101 A | * | 8/1999 | Kato et al. | 604/181 |
| 5,967,369 A | * | 10/1999 | Kafer et al. | 222/82 |
| 6,145,703 A | * | 11/2000 | Opperman | 222/82 |
| 6,290,679 B1 | * | 9/2001 | Hostettler et al. | 604/208 |
| 6,321,942 B1 | * | 11/2001 | Krampen et al. | 222/82 |
| 6,382,465 B1 | * | 5/2002 | Greiner-Perth | 222/309 |
| 6,387,074 B1 | * | 5/2002 | Horppu et al. | 206/221 |
| 6,419,656 B1 | * | 7/2002 | Vetter et al. | 604/90 |

* cited by examiner

DISCHARGE APPARATUS FOR MEDIA

The invention relates to a discharge apparatus for media in accordance with the preamble of claim 1 and such as is e.g. known from EP 245 895 A1. Such a discharge apparatus for media is particularly intended for the discharge of media containing at least one pharmaceutical substance.

With such discharge apparatuses the medium to be discharged is stored in a container having chambers separated from one another. Into each of the chambers is introduced a single medium component and the media components together give the medium to be discharged. The container is placed in a casing, which has a discharge opening for discharging the medium. An actuating means movable relative to the casing is provided. Through actuation of the actuating means firstly a connection is formed between the container chambers.

In the case of discharge apparatuses for media the media to be discharged are stored in a container. Media exist, which cannot be permanently stored and which are not permanently stable in their ready-to-use administration form. To make it possible to store such media over long periods, which in particular includes an appropriate time for intermediate storage, for the distribution of the medium produced via the manufacturer to the wholesaler and then to the retailer, e.g. pharmacies, together with an adequate consumption period of the medium, it has been proposed that the medium be separately stored in the form of individual, in each case stable or more stable media components and to effect the mixing of the media components immediately prior to application or use. As the mixing of the components usually requires a precise dosing of said components, this cannot be readily independently performed by a non-expert. Usually at least a trained person is needed to carry out this action and then subsequently administer the medium to the final consumer, i.e. the patient.

Examples of media which can be kept for longer periods broken down into the different partial components and which as a mixture are not permanently stable, frequently occur in connection with pharmaceutical applications. Particularly if part of the medium is a lyophilized powder (a so-called lyophilizate), which has to be dissolved in an aqueous carrier liquid or discharged together with the latter, the substance mixture is unstable. However, there are also numerous applications in which the two liquid media components when mixed are not stable, whereas each individually and separately can be stored for long periods.

A dispenser in which the media components are stored separately from one another in a container and are dischargeable together in mixed form is e.g. known from the preamble-forming EP 245 895 A1. In the case of such a dispenser an actuating means is provided in order to perform the mixing process of the media components and then discharge the medium. For mixing together the media components it is necessary to perform several pump strokes with the actuating means. At the end of the pump strokes and when the media components are fully mixed, there is a discharge stroke and during the latter the total medium quantity is discharged.

However, it is tedious that numerous pump strokes have to be performed in order to mix the media components.

It has proved that it can be advantageous to discharge a medium in several, clearly defined partial batches or charges. This is e.g. the case if the medium is to be administered nasally and a uniform quantity of medium is to be introduced into both nostrils. It has been found that e.g. when administering anticephalalgics a nasal application is advantageous, because it leads to a rapid absorption of the substance by the body. Simultaneously this makes it possible to administer substances, which otherwise in certain circumstances could not be administered in tablet form, but instead would have to be administered in spray form and therefore only by trained personnel. However, the application of such a medicament administration is not limited to anticephalalgics. It is also possible to administer nasally other forms of analgesics and further pharmaceutical substances. The only important factor is that the body can absorb the substance administered through the nose.

It is not known that prior to the performance of the partial discharges of the medium there must be a mixing process of the media components in order to produce the medium to be discharged.

Therefore the problem of the invention is to provide a discharge apparatus for media through which on the one hand the separate storage is possible of media components in separate chambers and on the other the medium to be discharged can be discharged in clearly defined partial charges.

On the basis of the preamble features, this problem is solved by the characterizing features of claim 1.

A discharge apparatus for media according to the invention and which is in particular intended for the discharge of a medium containing at least one pharmaceutical substance, has a container, which stores the medium in the form of media components, said media components being introduced into chambers separated from one another. Together the media components give the medium to be discharged. The container is located in a casing having a discharge opening for medium discharge purposes. An actuating means is possible, which is movable relative to the casing. This is also understood to cover an arrangement in which the container is placed indirectly in a sleeve, which is contained in the casing, the actuating means being movable relative to the sleeve. An actuation of the actuating means initially leads to the formation of a connection between the container chambers. The actuating path or course of the actuating means is, according to the invention, subdivided into a first partial actuating path and into a plurality, i.e. at least two, of following partial actuating paths. During the first actuating path the media components are mixed to form the medium to be discharged. With each of the following partial actuations of the actuating means is associated the preferably atomized discharge of a clearly defined partial charge of the medium. There are advantageously at least two and in particular two following partial actuations. However, it is also possible for there only to be one following partial actuation, i.e. all the medium to be discharged is discharged in a following partial actuation. It is appropriate if the first partial actuation and the first, following partial actuation takes place by means of an uninterrupted, continuous actuation of the actuating means. It is particularly advantageous with such a construction of the discharge apparatus that a plurality of partial actuations of the actuating means is unnecessary in order to mix the media components to form the medium and instead this can take place through a single partial actuation. The further actuations in each case serve to discharge a clearly defined partial charge.

According to an advantageous development of the invention the container chambers are separated from one another by plugs located in the container. It is also advantageous to form on the container overflow channels, which are positioned in such a way that during the first partial actuation of the actuating means the plugs separating the chambers from one another can be brought into a position in the vicinity of the overflow channels, so that the latter interconnect the chambers.

According to a preferred construction of the invention for subdividing the actuating path into partial actuating paths a connecting link guide is provided. The connecting link guide preferably has pressure point means and at the beginning of each following partial actuation it is necessary to overcome the pressure point means. Advantageously the connecting link guide has a linear guide portion for each partial actuation, the guide portions being so mutually displaced that they are in each case limited by a stop and that between two partial actuations it is necessary to perform a reversing actuation differing from the partial actuation. Preference is given to constructions in which at least the reversing actuation is automatically performed between two following partial actuations. Particular preference is given to constructions in which for the automatic performance of the reversing actuation force or tension reservoirs are provided, which are pretensioned when performing the preceding partial actuation.

According to a preferred development of the invention the container is placed in stable manner in a sleeve. The sleeve is movable relative to the casing and can be brought from a starting position into a discharge position. In the starting position the container is held in oriented manner by the sleeve in the discharge apparatus casing. The container is hermetically sealed. From this starting position the sleeve can be brought into the discharge position and during bringing into this position a fluidic connection is produced between the first chamber oriented towards the discharge opening of the discharge apparatus. Preferably the bringing of the sleeve from the starting position into the discharge position takes place during the first partial actuation. For producing the fluidic connection between the first chamber and the discharge opening a container-side terminal plug, which is preferably fixed to the container with a crimp closure, is perforated by a casing-side needle having a discharge channel.

Advantageously the connecting link guide is constructed between the sleeve and the actuating means and preferably the at least one sliding block is constructed on the actuating means and the at least one link path of the link guide is constructed on the sleeve.

It is also advantageous if the reversing actuation takes place between the first partial actuation and the first, following partial actuation by rotating or twisting the actuating means with respect to the casing or, if provided, with respect to a sleeve located in the casing and preferably the rotation angle is predetermined by stop edges of the connecting link guide and in which preferably a rotation of the sleeve with respect to the casing is prevented by means of a tooth system.

It is also advantageous if the container has a first chamber facing the discharge opening of the discharge apparatus and at least one further chamber. The chambers are preferably separated from one another by plugs axially displaceable in the container. The last of the chambers is also sealed with a plug and the actuating means acts thereon.

According to an advantageous development the first chamber facing the discharge opening has a volume with a gas bubble and during the first partial actuation by compression of the gas bubble it is possible to produce a frictional connection between the actuating means and the container, by means of which the container can be brought from the starting position, where the container is preferably hermetically sealed, into the discharge position, where a fluidic connection is produced between the discharge opening and the first chamber. With such a construction on producing the fluidic connection the frictional connection by means of the gas bubble is interrupted, i.e. in simple manner a path-controlled frictional connection is produced. Alternatively or additionally it is also possible that the stop limiting the first partial actuation is constructed in such a way that the container is brought into a discharge position, where the fluidic connection between the first chamber and the discharge opening is produced.

Preference is given to constructions in which the container has two chambers and into the first chamber is preferably introduced a dry, particularly soluble media component, such as a lyophilizate and into the second chamber is introduced a carrier medium, preferably an in particular liquid solvent as the media component. It is also advantageous if two following partial actuations bringing about an equal discharge can be performed.

These and further features can be gathered from the claims, description and drawings and the individual features, both singly and in the form of subcombinations can be implemented in an embodiment of the invention and in other fields and can represent advantageous, independently protectable constructions for which protection is hereby claimed.

Figure 1:
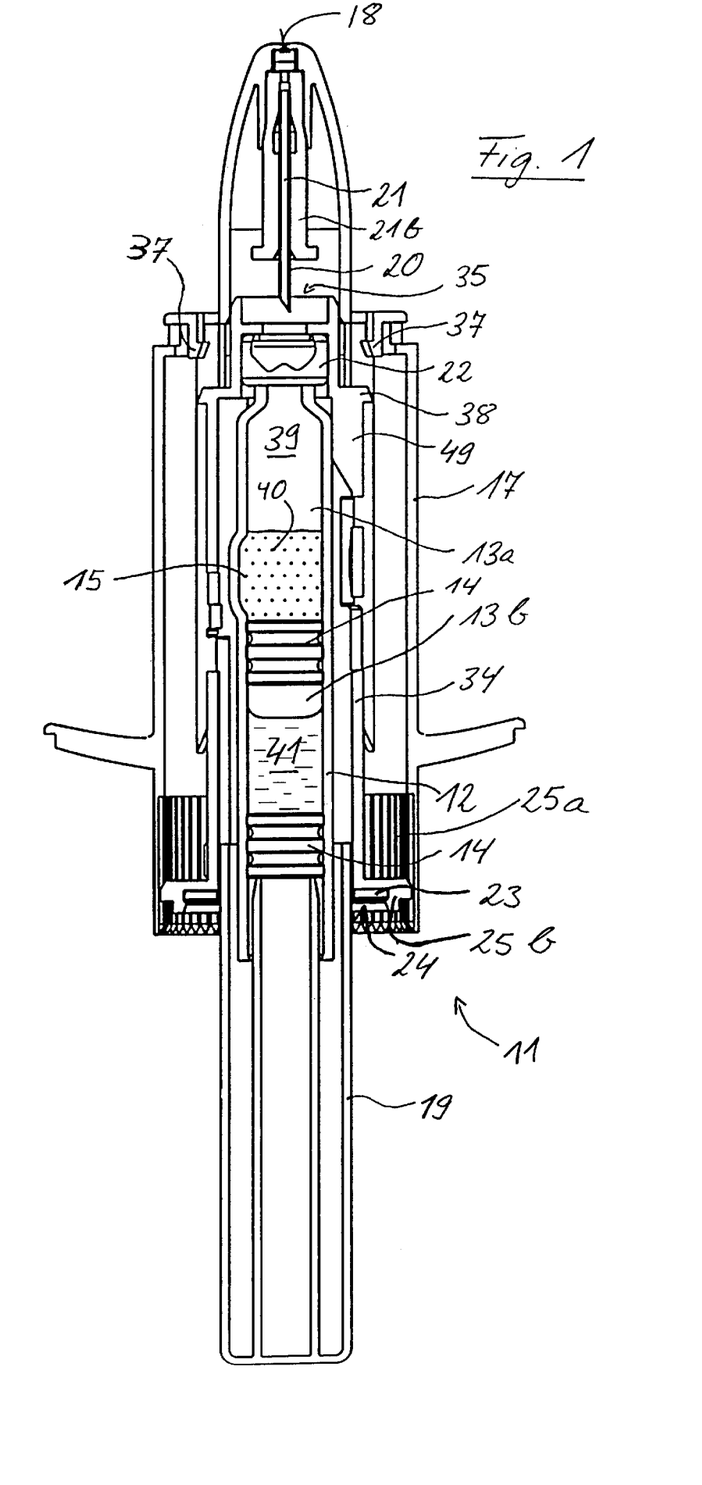
FIG. 1 A sectional representation of an unactuated discharge apparatus according to the invention.
Figure 2:
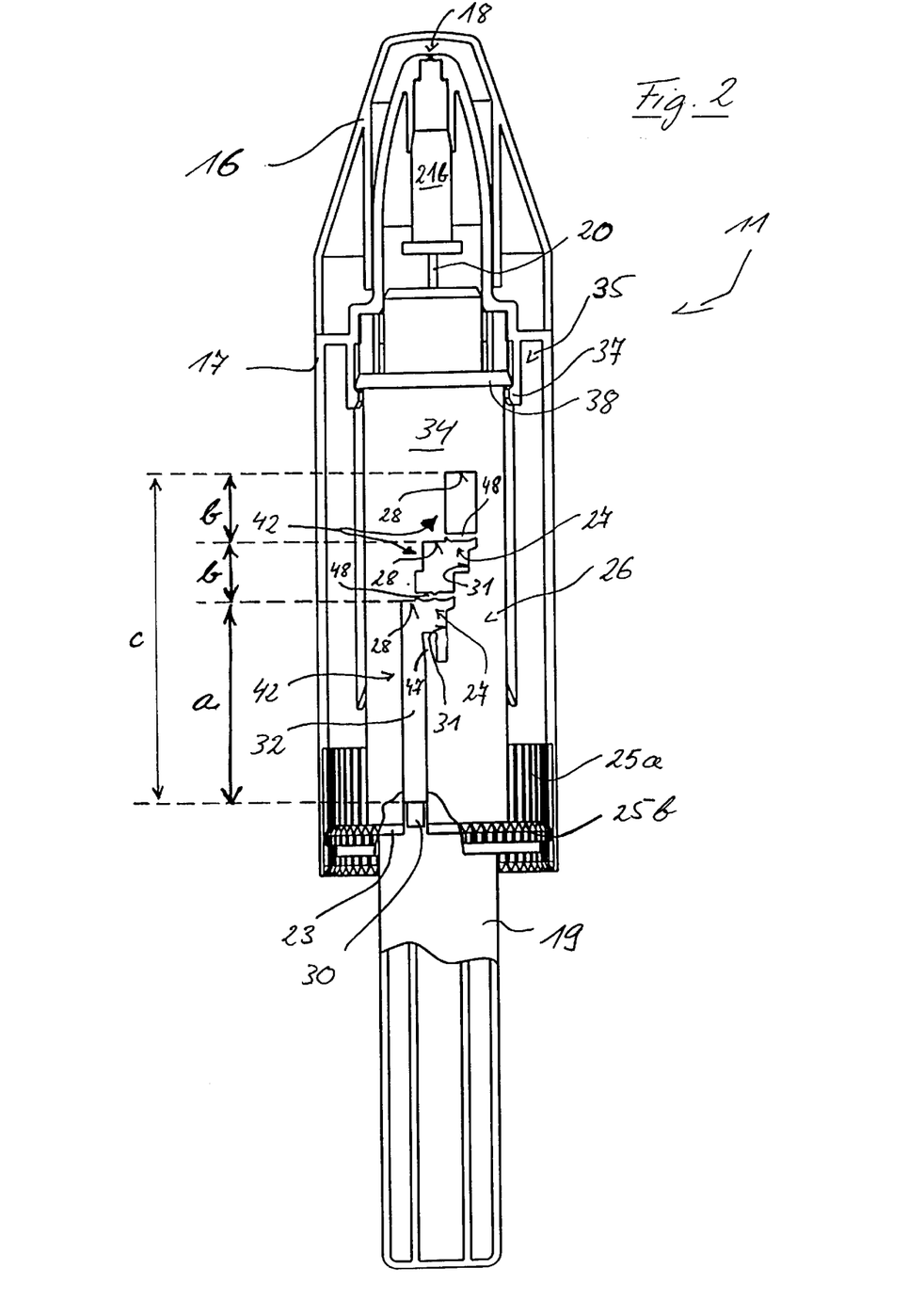
FIG. 2 A part sectional side view of an unactuated discharge apparatus according to the invention.
Figure 3:
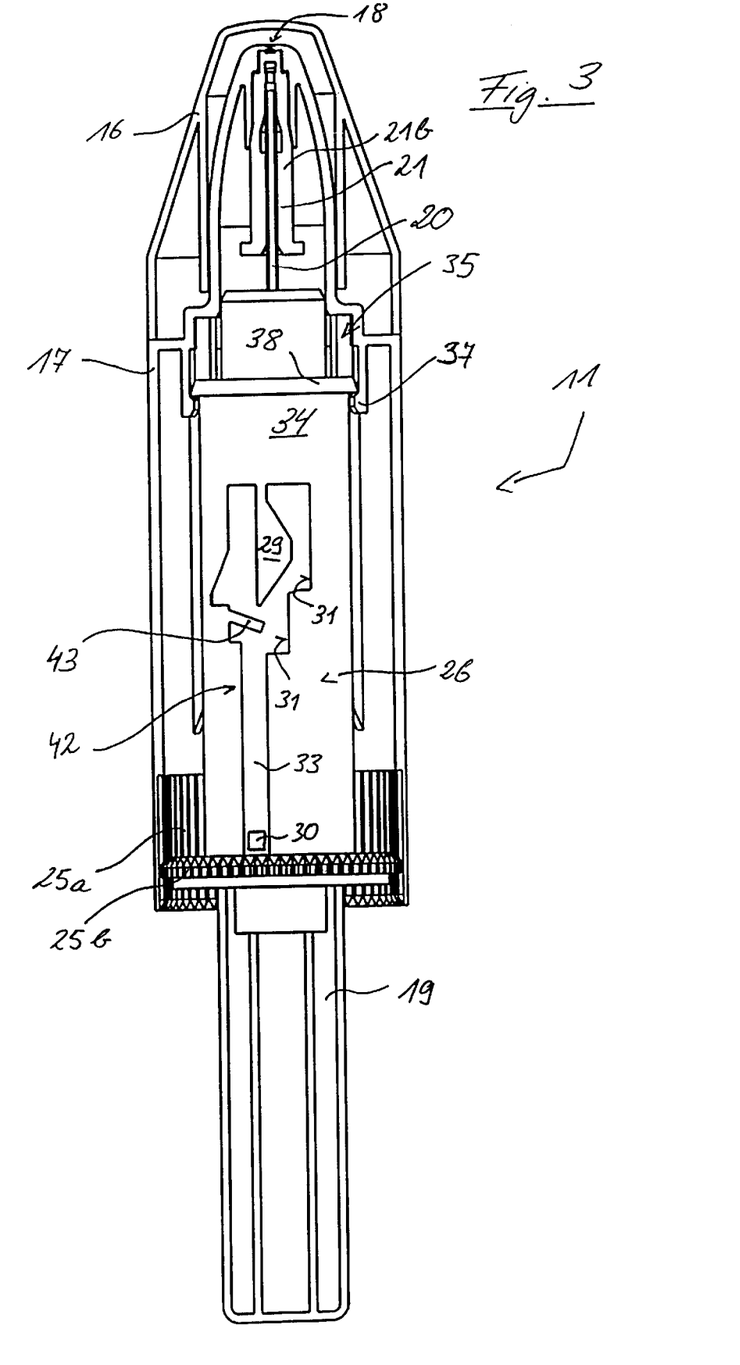
FIG. 3 A part sectional representation of the discharge apparatus of FIG. 2 from the opposite side.

An embodiment is described hereinafter relative to the attached drawings, wherein show:

FIGS. 1 to 3 show a dispenser according to the invention in its unactuated starting position.

FIG. 1 shows a sectional view through the discharge apparatus according to the invention. The discharge apparatus 11 has a casing 17 with a discharge opening 18 for discharging the medium. The casing contains a needle 20, e.g. by means of a filler 21b, which is able to form the discharge channel 21 between a first chamber 13a of a container 12 and the discharge opening 18. On the casing 17 are formed inwardly projecting detents 37, which can engage behind a locking ring 38 of a sleeve 37 and are consequently suitable for establishing a clearly defined discharge position of the sleeve 37 in the casing 17. The casing 17 also contains the actuating means 19, which are in the form of concentrically arranged tubular portions comprising two hollow cylindrical elements and which are terminated at the lower end by a common actuating surface. The actuating surface is constructed substantially radially to the extension of the tubular portions and is manually operable. The tubular portions have different lengths. The diameter of the inner tubular portion is such that it can be introduced into the container 12. The outer tubular portions, whose axial extension is preferably longer than that of the inner tubular portion, slides along the sleeve 34. Between the sleeve 34 and actuating means 19 is formed a connecting link guide shown in FIGS. 2 and 3.

The casing 17 contains the sleeve 34, which receives the medium for the container 12. If the container 12 is closed at its front end by a crimp closure 22, the container 12 can easily be fixed in the sleeve 34 in that on the sleeve 34 is formed a locking means for the crimp closure 22. Alternatively or additionally it is possible to provide in the sleeve 34 ribs 49, which project inwards towards the container 12 and at least in the upper area of said container 12 representing e.g. 5 to 10 mm, retains the same in clamping manner. Preferably three ribs 49 are provided for this purpose. This makes it possible to hold the container 12 in stable manner in the sleeve 34. In addition, the sleeve also extends over at least part of the axial length of the container 12. In the represented embodiment the sleeve 34 extends almost to the rear end of the casing 17. In order to ensure a twist-proof mounting of the sleeve 34 in the casing 17, the latter has on its inside tooth system 25a extending over an axial portion. A tooth system 25b on the sleeve engages in said tooth system 25a on the casing. The tooth systems 25a, 25b, as a result of their mutual engagement, ensure that the sleeve 34 does not twist with respect to the casing 17. However, it is simultaneously possible for the sleeve 34 to perform an axial movement in the casing 17. The lengths of the tooth systems must be such that the sleeve 34 can be brought from the starting position 35 shown into the discharge position and in spite of this the tooth systems remain in mutual engagement and do not protude.

The container 12 is located in the sleeve 34. The container 12 is e.g. held in the sleeve 34 by means of the crimp sleeve of the crimp closure 22. The container 12 is preferably a glass container. Such containers are e.g. capsules or carpules. In place of glass containers plastic containers can be used. The container only has to satisfy the requirements regarding tightness, sterility, stability and strength, whilst also be easy to manufacture. The container 12 has two chambers, namely a first chamber 13a and further chambers 13b. The two chambers are separated from one another by a plug 14. In the represented starting position, the plug is in a position where it completely separates the two chambers from one another. The plug 14 is axially displaceable in the container 12. It can be brought into a position where it is located in the vicinity of an overflow channel 15. In this case a connection is produced between the two chambers 13a, 13b. The overflow channel 15, which is in particular constructed as a bypass, for this purpose has a length somewhat exceeding the axial length of the plug 14. On the front side facing the discharge opening 18 of the discharge apparatus 11 the container 12 is closed by a crimp closure 22. In the case of such a crimp closure a plug, which is placed in sealing manner in the opening of the container 12, is held by a crimp ring and partially pressed onto the container 12. In turn, the crimp ring is held on a coupling edge of the container 12, which is constructed to fulfil this requirement. The plug is usually made from a rubbery material, so that the plug braces the crimp ring with respect to the coupling edge. This makes it possible to create a strong, good sealing closure of the container 12. At its rear end the last, further chamber 13b is also closed by a plug 14. In the same way as the plug 14 separating the two chambers from one another, said plug 14 is also arranged in axially movable manner in the container 12. However, a hermetic seal of the chamber is ensured by the plug 14. The inner tubular portion of the actuating means 19 can act on said plug 14 and to this end, even in the unactuated starting position shown in FIG. 1, can engage on said plug 14.

Into the first chamber 13a is introduced a media component, e.g. the lyophilizate 40. Into the first chamber is introduced precisely the media component quantity necessary for the discharge of the desired number of partial charges. A very precise dosing of the media component quantity is possible. The first chamber 13a also contains a gas bubble 39, which can in particular be formed by an inert gas, pure room air or normal ambient air. It can be advantageous to subsequently sterilize the filled carpule and also the gas. The gas should be free from any type of admixture or impurity. It must in particular be ensured that the gas of the gas bubble does not react with the media component introduced into the chamber 13a in such a way that its effectiveness or stability is destroyed.

The remaining media components are housed in the further chambers 13b and in the represented embodiment there is only one further chamber 13b. In the represented embodiment a carrier medium 41 is introduced into the further chamber 13b. The carrier medium 41 is in particular a solvent for the lyophilizate 40. Preferably the further chamber 13b is filled as completely as possible with the carrier medium 41. According to the embodiment shown this is a non-compressible or only slightly compressible liquid. Here again it must be ensured that the media component is not contaminated by any residual air present or by any other substance introduced or contamination present in the container. However, this can be ensured by conventional manufacturing and filling methods. The carrier medium 41 is preferably water or aqueous solutions, such as e.g. alcohol-containing solutions. Water-based carrier media 41 are generally suitable for dissolving or absorbing the lyophilizate 40 in such a way that there is a uniform thorough mixing of the carrier medium with the lyophilizate 40 or the other media components introduced into the first chamber.

FIGS. 2 and 3 show, in each case in part sectional form, the discharge apparatus of FIG. 1 from two opposite sides. Unlike in FIG. 1, the sleeve 34 is shown in a substantially uncut form, so that the construction of the connecting link guide 26 between the actuating means 19 and the sleeve 34 is visible.

According to FIGS. 2 and 3 the discharge apparatus 11 is closed with a removable protective cap 16, which protects the discharge opening 18 against contamination. The protective cap 16 is preferably constructed in such a way that it simultaneously fulfils a childproof protection function. This takes place e.g. in that the protective cap can be gripped at certain points and has to be slightly compressed in order to remove it from the casing 18. It can simultaneously be provided that an actuating barrier acts between the protective cap 16 and the actuating means 19 or sleeve 34. The actuating barrier must prevent an actuation of the actuating means 19 for as long as the protective cap 16 is fitted on the discharge apparatus 11.

The sleeve 34 is held in the casing 17 of the discharge apparatus 11 and is located in the starting position 35. The sleeve 34 is held in the starting position 35 by detents 37, which engage behind the locking ring 38. The sleeve 34 is axially displaceable towards the discharge opening 18 and at the end of this displacement path enters the not shown discharge position. By means of the tooth system 25a, 25b on the inside of the casing 17 or on the sleeve 34 respectively, it is ensured that the sleeve 34 cannot be twisted in the casing 17. Between the actuating means 19, which is also held in guided manner in the casing 17 or sleeve 34 guidance preferably taking place through the sleeve 34 and the container 12, a connecting link guide 26 is formed. The connecting link guide is formed by link paths 32, 33, which according to the embodiment shown are formed in the sleeve 34, as well as sliding blocks 30 guided therein and which are shaped on the actuating means 19.

In the sleeve 34 is constructed a first link path 32 and on the facing side shown in FIG. 3 a second link path 33, the two link paths having different functions. The first link path 32 serves to subdivide the actuating path c of the actuating means 19 into the first partial actuating path a and the following partial actuating paths b. The function of the second link path 33 is essentially to perform the automatic reversing actuation between the further partial actuations. In the represented embodiment the reversing actuation takes place manually and not automatically between the first partial actuation a and the first, following partial actuation b.

However, through a corresponding construction of the second link path 33 it would be possible for said reversing actuation to take place automatically. An advantage of a manual reversing actuation at this time is that it is necessary or at least desirable for achieving a good thorough mixing between the media components for forming the medium to be discharged, for the discharge apparatus 11 to be shaken, before the following partial actuations are performed and with which a discharge of medium is associated.

The first link path 32, in which the actuation means-side sliding block 30 is guided, subdivides the actuating path c of the actuating means 19 into a first partial actuating path a and several following partial actuating paths b and in which in each case a following partial actuation is associated with the first partial actuating path of the first partial actuation and the following partial actuating paths b. The subdivision of the actuating path c into partial actuating paths takes place through in each case a stop 28, which is constructed at the end of a linear guide portion 42 associated with the partial actuating path. For this purpose the linear guide portions 42 are displaced in step-like manner. In the vicinity of the stop 28 such a wide portion is formed that the sliding block 30 can be oriented by rotating the actuating means 19 relative to the sleeve 34 and consequently the casing 17 relative to the following, linear guide portion 42. The rotating path is limited by a stop 31. At the start of at least each following partial actuating path b pressure point means 27 acting on the sliding block 30 are formed. The pressure point means ensure that at the start of the actuation process the actuating force of the actuating means 19 exceeds a threshold value, so that the complete performance of a partial actuation is always ensured. In the represented embodiment material webs 48 are formed for this purpose at the start of the partial actuating paths and have at least one predetermined breaking point and which are broken on exceeding the minimum force. To ensure that at the start of performing the first partial actuation an adequate actuating force for this purpose acts on the actuating means 19, it can be provided that, as shown in FIG. 1, a retaining ring 23 is provided on the casing or on sleeve 34, which is supported there and connected by predetermined breaking points 24 to the actuating means 19. Thus, the first partial actuation can only take place when the minimum force necessary for said first partial actuation is exceeded.

The second link path 33 shown in FIG. 3 and in which is also guided a sliding block 30 connected to the actuating means 19 has a different function. During the first partial actuation only the sliding block 30 is guided in the linear guide portion 42. After performing the first reversing actuation, i.e. the reversing actuation between the first partial actuating path and the first following partial actuating path, the non-reversing lock 43 projecting into the link path serves to ensure that a rotating back of the actuating means 19 from the starting position for the first following partial actuation does not take place. In the second link path 33 is formed a stop 31, which serves as an end position definition for the reversing actuation. During the following partial actuations a force or tension reservoir 29 projecting into the linear guide portion is displaced from the latter. The deformation energy of the elastic deformation of the tension reservoir 29 is used for performing the following reversing actuation. For producing the pretension and ensuring that there is no premature performance of the reversing actuation before reaching the end position of the particular partial actuation, the first link path 32 shown in FIG. 2 is provided.

With respect to the starting position shown in FIGS. 1 to 3 an explanation is also provided of the performance of a complete actuation of the discharge apparatus.

At the start of actuation the protective cap 16 must be removed. It is also possible to raise an actuation barrier for the actuating means 19. Simultaneously a position securing protection for maintaining the starting position 35 for the sleeve 34 with the container 12 held therein can be removed, so that the container 12 together with the sleeve 34 can be brought into the discharge position defined by the detents 37.

To permit a mixing of the media components of the first chamber 13a with the media component of the further chamber 13b, i.e. the carrier medium 41, force-urged in the direction of the discharge opening 18, the actuating means 19 must be moved into the casing 17. The predetermined breaking points 24 between the actuating means 19 and retaining ring 23 break. The sliding blocks 30 slide in the connecting link guide 26 with the two link paths 32, 33. As a result of the necessary minimum actuating force for overcoming the breaking forces of the predetermined breaking point 24 there is a complete, first partial actuation over the entire first partial actuating path a up to the reaching of the stop 28 at the end of the first, linear guide portion 42 of the first link path 32. The withdrawal barrier 47 of the first link path 32 prevents a sliding back or withdrawal of the actuating means 19. During this stroke movement the plug 14 at the end of the container and which is frictionally connected to the actuating means 19 is shoved towards the discharge opening 18. As a result of the incompressible liquid, i.e. carrier medium 41, located in the further chamber 13b, the central plug 14, which separates the first chamber 13a from the further chamber 13b, is also shoved forwards in the direction of the discharge opening 18. This movement of the plug 14 between the two chambers 13a, 13b continues until the carrier medium 41 can flow past said plug 14 through the overflow channel 15 into the first chamber 13a. Simultaneously with the movement of the plug 14 between the two chambers 13a, 13b the lyophilizate 40, which is located in the first chamber 13a, is moved forwards, i.e. in the direction of the discharge opening 18. As a result of the inflowing carrier medium 41 the lyophilizate 40 is slowly dissolved. The dischargeable medium results from the two media components.

During this first partial actuation over and beyond the first partial actuating path a an overpressure builds up in the first chamber 13a, because the total reception volume of the container 12 is continuously reduced. Into the first chamber 13a flows the carrier medium 41 of the further chamber 13b, whose own volume is slowly reduced to zero. Thus, a continuously rising pressure is built up in the gas bubble 39 of the first chamber 13a. This pressure becomes so large that it prevents the further movement of the plug 14 in the container 12. This leads to a frictional connection between the actuating means 19 and the sleeve 34, so that the complete container 12 is moved forwards in the direction of the discharge opening 18 by means of the sleeve 34, in which the container 12 is held in stable manner. The plug located in the crimp closure 22 is slowly perforated by the tip of the needle 20. As soon as the container closure has been completely perforated by the needle 20 and consequently by means of the discharge channel 21 of the needle 20 a fluidic connection is formed between the first chamber 13a and the discharge opening 18, the overpressure can escape from the first chamber 13a and the frictional connection between the sleeve 34 and actuating means 19 is interrupted. The sliding block 30, which is guided in the first link path 32, comes into engagement with the stop 28. It is now pressed further and consequently the sleeve 34, together with the container 12 held therein, is shoved further forwards until the detents 37 engage behind the locking ring 38. In this position the discharge position of sleeve 34 and the container 12 held therein is reached. The sleeve 34 is now stable with respect to the discharge apparatus casing 17. This effectively prevents a retraction of the sleeve 34. As yet no medium has been discharged from the first chamber 13a and only the gas of the gas bubble has been displaced.

Since in this position the withdrawal barrier 47 prevents the drawing back of the sliding block 30 of the first link path 32, the container 17 can be shaken in this position for producing the medium and for a good thorough mixing or good dissolving in or with one another of the media components. In this position the rear plug 14 is moved completely up to the front plug 14, so that the volume of the further chamber 13b is reduced to zero and the entire carrier medium 41 is moved into the first chamber 13a.

To perform the first, following partial actuation, i.e. the first discharge of medium through the discharge opening 18, the discharge apparatus must be introduced at the application location. For example, the casing 17 with the discharge opening 18 must be introduced into one of the two nostrils of a patient. Now or even before the application of the discharge apparatus to the patient, the actuating means 19 must be turned clockwise up to the stop 31 of the two link paths 32, 33 of the connecting link guide 26. After completing this reversing actuation, a turning back is prevented by the non-reversing lock 43 of the second link path 33. The tooth systems 25a, 25b between sleeve 34 and casing 17 prevent an accidental rotation of the sleeve 34 in the casing 17. The first, following partial actuation, over and beyond the following partial actuating path b, now takes place by the application of an actuating force to the actuating means 19, which acts on their bottom and is directed towards the discharge opening 18. It is necessary to overcome the pressure point means 27 of the first link path, which is in the form of a material web 48 formed at the beginning of the associated linear guide portion 42. The pressure point means preferably have predetermined breaking points. It is then ensured that an actuation is performed which extends over the entire partial actuating path b of the following partial actuation and which is in turn defined by the corresponding stop 28 in the first link path 32. During this movement the tension reservoir 29 is pushed aside on the opposite side in the second link path. As a result of the elastic deformation of the tension reservoir 29 a pretensioning thereof is obtained and is used for the following reversing actuation, which takes place before the second, following partial actuation.

During the first, following partial actuation a corresponding medium quantity, which is formed from the two media components, is displaced from the first chamber 13a through the discharge channel 21 of the needle 20 and reaches the discharge opening 18, where the medium is atomized and discharged.

Before performing the second, last, following partial actuation the actuating force on the actuating means 19 must be reduced. This reduces the contact pressure of the sliding block 30 on the stop 28. The pretensioned tension reservoir 29 now further rotates the sleeve 34 until the sliding block 30 reaches the next stop 31. The tension reservoir 29 is then relaxed, the sliding block 30 of the first link path 32 is directly in front of the second pressure point means 27 and the final, linear guide portion 42. The second application stroke takes place by again actuating the actuating means 19 in the same way and with the same effect as in the first, following partial actuation. Here again a pressure point means 27 is destroyed. A discharge of medium from the first chamber 13a is brought about by further displacement of the two plugs 14 of container 12 in the direction of discharge opening 18. The discharge media volume is determined by the actuating path of the following partial actuation, here both during the first partial actuation and during the second partial actuation of the partial actuating path b. The container, an ampoule, capsule or carpule is now emptied. Relevant parts of the discharge apparatus are destroyed after use and cannot be reused. It is consequently a disposable system and can then be supplied to recycling. It is advantageous to make the discharge apparatus mainly from plastic, which can consequently be chosen in type-pure manner. According to a preferred development only the crimp closure and needle are constructed as metallic parts and optionally the crimp closure is also made from plastic. The plugs 14 are frequently made from an elastomer or rubber and can be recycled. Thus, it is a particular advantage of such a construction of the discharge apparatus that only a small number of different materials are used, accompanied by a small number of metallic components. There are no metallic springs, pins or other such elements, apart from those referred to hereinbefore. After removing the protective cap the discharge apparatus is ready for the mixing of the media components, i.e. for performing the first partial actuation. The actuating means must then be turned clockwise. This manual further turning can also be replaced by an automatic turning. The discharge apparatus is then ready for use. The following partial actuations for discharging the medium can directly succeed one another and be performed without any additional manual movements. Despite the necessary mixing of the medium from the media components, the discharge apparatus is easy to handle. This easy handling is an essential advantage of the invention.

What is claimed is:

1. Discharge apparatus for media, in which
   the media to be discharged is stored in a container (12), which has first and second chambers 13a 13b separated from one another and into which is introduced respective media components,
   when mixed together the media components providing the media to be discharged,
   the container being placed in a casing having a discharge opening for discharging the media,
   a means for actuating the apparatus, said means for actuating being movable relative to the casing, and
   in which through actuation of the means for actuating firstly a connection between the chambers of the container is produced,
   wherein an actuating path (c) of the means for actuating (19) is subdivided into a first partial actuating path (a) and at least two of further partial actuating paths (b) and during the first partial actuating path (a) the media components (40, 41) are mixed to form the media to be discharged and in which with each following partial actuation of the means for actuating (19) is associated the discharge of a clearly defined partial charge of the media,
   wherein a connecting link guide (26) is provided for subdividing the actuating path (c) into the partial actuating paths (a, b), and
   wherein the connecting link guide (26) for each partial actuation has a linear guide portion (42), the guide portions (42) being so mutually displaced that they are in each case limited by a stop (28) and between two partial actuations a reversing actuation differing from the partial actuation is to be performed.

2. Discharge apparatus according to claim 1, wherein the chambers (13a, 13b) are separated from one another by means of plugs (14) located in the container (12).

3. Discharge apparatus according to claim 1, wherein the container (12) has overflow channels (15) and during the first partial actuation (a) plugs (14) separating the chambers (13a, 13b) from one another can be brought into a position in the vicinity of the overflow channels (15), so that the chambers 13a 13b are interconnected by means of the overflow channels (15).

4. Discharge apparatus according to claim 1, wherein a connecting link guide (26) is provided for subdividing the actuating path (c) into the partial actuating paths (a, b).

5. Discharge apparatus according to claim 4, wherein the connecting link guide (26) has means (27) for defining a pressure point, which have to be overcome at the start of each following partial actuation.

6. Discharge apparatus according to claim 1, wherein two successive partial actuations (b) bringing about an equal discharge can be performed.

7. Discharge apparatus according to claim 1, wherein at least the reversing actuations are automatically performed between two following partial actuations (b).

8. Discharge apparatus according to claim 7, wherein tension reservoirs (29) are provided and are pretensioned during the performance of a partial actuation and serve to subsequently automatically perform the reversing actuation.

9. Discharge apparatus according to claim 1, wherein the reversing actuation between the first partial actuation (a) and the first, following partial actuation (b) takes place by rotating the means for actuating relative to the casing (12), an angle of said rotation being predetermined by stop edges (31) of the connecting link guide (26).

10. Discharge apparatus according to claim 9 in which by means of a tooth system (25a, 25b) a rotation of a sleeve (34) relative to the casing (17) is blocked.

11. Discharge apparatus according to claim 1, wherein the discharge is an atomized discharge.

12. Discharge apparatus according to claim 1, wherein the media contains at least one pharmaceutical substance.

13. Discharge apparatus for media, in which
the media to be discharged is stored in a container, which has first and second chambers separated from one another and into which is introduced respective media components,
when mixed together the media components providing the media to be discharged,
the container being placed in a casing having a discharge opening for discharging the media,
means for actuating the apparatus, said means for actuating being movable relative to the casing, and
in which through actuation of the means for actuating firstly a connection between the chambers of the container is produced,
wherein an actuating path (c) of the means for actuating (19) is subdivided into a first partial actuating path (a) and at least two of further partial actuating paths (b) and during the first partial actuating path (a) the media components (40, 41) are mixed to form the media to be discharged and in which with each following partial actuation of the actuating means (19) is associated the discharge of a clearly defined partial charge of the media, and
wherein the container (12) is placed in stable manner in a sleeve (34), which is movable relative to the casing (17) and can be brought from a starting position (35) into a discharge position and in said discharge position a fluid connection is formed between a first chamber (13a) of the container and the discharge opening (18).

14. Discharge apparatus according to claim 13, wherein the bringing of the sleeve (34) from the starting position (35) into the discharge position takes place during the first partial actuation (a) and for producing the fluidic connection between the discharge opening (18) and the first chamber (13a) of the container (12) a casing-side needle having a discharge channel (21) perforates a container-side plug.

15. Discharge apparatus according to claim 13, wherein the connection link guide (26) is constructed between the sleeve (34) and means for actuating (19) at least one sliding block (30) is constructed on the connecting means (19) and the at least one link path (32, 33) of the connecting link guide (26) on the sleeve (34).

16. Discharge apparatus according to claim 13, wherein the container (12) has a first chamber (13a) facing the discharge opening (18) of the discharge apparatus (11) and at least one further chamber (13b), and which are provided with a plug (14) axially displaceable in the container, for separating and closing the chambers, as well as a plug (14) closing the last of the chambers (13b) and on which acts the means for actuating (19).

17. Discharge apparatus for media, which has first and second chambers separated from one another and into which are introduced first and second media components respectively, when mixed together the media components providing a mixed media to be discharged, the container being placed in a casing having a discharge opening for discharging the media, means for sealing being provided for tightly sealing the container at a side facing the discharge opening, means for opening being provided and being located between the means for sealing and the discharge opening for opening the means for sealing and for connecting the second chamber with the discharge opening, means for actuating the apparatus being moveable relative to the casing and in which through actuation of the means for actuating firstly a connection between the first and second chambers of the container is opened to transfer said first media component from the first chamber to the second chamber and to mix the first and the second media component wherein an actuation path (c) of the means for actuating (19) is subdivided into a first partial actuating path (a) being a mixing path and at least two further partial actuating paths (b) being a mixing path and at least two further partial actuating paths (b) being partial discharge paths during the first actuating path (a) the media components (40, 41) are mixed to form the mixed media to be discharged and the means for sealing being opened by the means for opening due to the actuation of the means for actuating, while during each following partial actuation of the means for actuating (19) a clearly defined partial charge of the mixed media is discharged, and
wherein the first chamber (13a) facing the discharge opening (18) has a volume with a gas bubble (39) and during the first partial actuation (a) by the compression of the gas bubble (19) a frictional connection can be formed between the actuating means (19) and container (12), wherein the container (12) can be brought from a starting position (35), and wherein the container (12) is preferably hermetically sealed, into a discharge position, in which a fluidic connection is produced between the discharge opening (18) and the first chamber (13a).

18. Discharge apparatus according to claim 17, wherein into the first chamber (13a) is preferably introduced a dry component.

19. Discharge apparatus according to claim 18, wherein the component is a soluble media component.

20. Discharge apparatus according to claim 19, wherein the component is a lyophilizate (40).

21. Discharge apparatus according to claim 18, wherein into the second chamber (13b) is introduced a carrier medium (41) as a media component.

22. Discharge apparatus according to claim 21, wherein the carrier media is a liquid solvent.

23. Discharge apparatus for media, which has first and second chambers separated from one another and into which are introduced first and second media components respectively, when mixed together the media components providing a mixed media to be discharged, the container being placed in a casing having a discharge opening for discharging the media, means for sealing being provided for tightly sealing the container at a side facing the discharge opening, means for opening being provided and being located between the means for sealing and the discharge opening for opening the means for sealing and for connecting the second chamber with the discharge opening, a means for actuating the apparatus being moveable relative to the casing and in which through actuation of the means for actuating firstly a connection between the first and second chambers of the container is opened to transfer said first media component from the first chamber to the second chamber and to mix the first and the second media component wherein an actuation path (c) of the means for actuating (19) is subdivided into a first partial actuating path (a) being a mixing path and at least two further partial actuating paths (b) being a mixing path and at least two further partial actuating paths (b) being partial discharge paths during the first actuating path (a) the media components (40, 41) are mixed to form the mixed media to be discharged and the means for sealing being opened by the means for opening due to the actuation of the means for actuating, while during each following partial actuation of the means for actuating (19) a clearly defined partial charge of the mixed media is discharged, and wherein during the first partial actuating path a bubble of compressed air is in the second chamber due to the transfer of a first one of the media components to the second chamber, which gas is vented through the discharge opening upon opening of the means for sealing without discharging said mixed media.

24. Discharge apparatus according to claim 23, wherein the means for opening is a hollow needle provided to pierce the means for sealing.

\* \* \* \* \*